United States Patent [19]
Achard et al.

[11] Patent Number: 5,484,942
[45] Date of Patent: Jan. 16, 1996

[54] THIOPYRANOPYRROLE DERIVATIVES

[75] Inventors: Daniel Achard, Thiais; Claude Moutonnier, Les Plessis Robinson; Jean-François Peyronel, Palaiseau; Michel Tabart, Paris; Alain Truchon, Lyon, all of France

[73] Assignee: Rhone-Poulenc Rorer S.A., Antony, France

[21] Appl. No.: 146,144

[22] PCT Filed: May 15, 1992

[86] PCT No.: PCT/FR92/00432

§ 371 Date: Nov. 17, 1993

§ 102(e) Date: Nov. 17, 1993

[87] PCT Pub. No.: WO92/20686

PCT Pub. Date: Nov. 26, 1992

[30] Foreign Application Priority Data

May 17, 1991 [FR] France ................ 91 06038

[51] Int. Cl.⁶ ............................................. C07D 495/04
[52] U.S. Cl. ............................................. 548/453
[58] Field of Search ................................. 548/453

[56] References Cited

U.S. PATENT DOCUMENTS

| | | | |
|---|---|---|---|
| 4,042,707 | 8/1977 | Ripka | 424/274 |
| 4,503,043 | 3/1985 | Blankley | 514/10 |
| 5,017,708 | 5/1991 | Ogata et al. | 548/515 |

FOREIGN PATENT DOCUMENTS

| | | |
|---|---|---|
| 0058567 | 8/1982 | European Pat. Off. . |
| 0068822 | 1/1983 | European Pat. Off. . |
| 0093805 | 11/1983 | European Pat. Off. . |
| 0359172 | 3/1990 | European Pat. Off. . |

*Primary Examiner*—David B. Springer
*Attorney, Agent, or Firm*—Finnegan, Henderson, Farabow, Garrett & Dunner

[57] ABSTRACT

This invention relates to novel derivatives of thiopyranopyrrole of general formula (I):

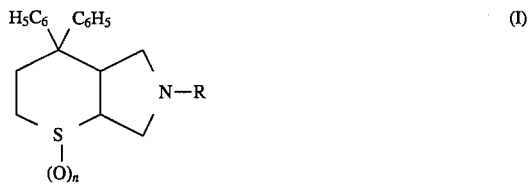

in which R is hydrogen, allyl, or a radical having the structure: —$CR_aR_bR_c$ where $R_a$ and $R_b$ are hydrogen atoms or phenyl radicals optionally substituted (by halogen, alkyl, alkyloxy or nitro), and $R_c$ is defined as $R_a$ and $R_b$ or stands for an alkyl or alkyloxyalkyl radical, at least one of $R_a$, $R_b$ and $R_c$ being a substituted or unsubstituted phenyl radical, and n is 0 to 2, in their stereoisomer forms, and mixtures thereof, and possibly the salts if they exist, and preparation thereof. The novel derivatives of the invention are particularly interesting as synthesis intermediates.

6 Claims, No Drawings

THIOPYRANOPYRROLE DERIVATIVES

FIELD OF THE INVENTION

The present invention relates to new thiopyranopyrrole derivatives of general formula:

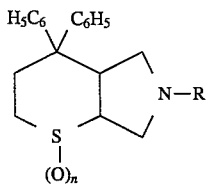

as well as their salts, when these exist, useful as intermediates in the preparation of thiopyranopyrrole derivatives, which are antagonists of the effects of substance P.

BACKGROUND OF THE INVENTION

Products derived from the isoindole of general formula:

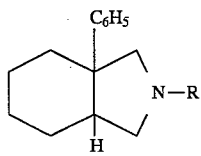

which exhibit an opium activity, have been described in American U.S. Pat. No. 4,042,707.

These products exhibit no activity towards substance P and nor are they used in the synthesis of such products.

Herbicides of the general formula:

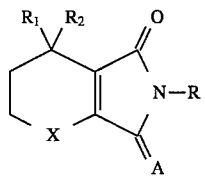

in which X may be a sulphur atom, $R_1$ and $R_2$ are hydrogen or alkyl and R is a substituted phenyl, have been described in European Application 0,068,822.

In spite of the research activities carried out and in spite of the interest created [M. R. Hanley, TINS, (5) 139 (1982)], practically no product has been discovered so far which acts specifically on substance P and has a nonpeptide structure, accordingly, the thiopyranopyrrole derivatives of general formula (I) are of great interest in so far as they make it possible to obtain such products.

DESCRIPTION OF THE INVENTION

In the general formula (I), the symbol R represents a hydrogen atom, an allyl radical or a radical of the structure:

 (Ia)

in which $R_a$ and $R_b$ are hydrogen atoms or phenyl radicals which are optionally substituted (by a halogen atom, an alkyl, alkoxy or nitro radical), and $R_c$ is defined as $R_a$ and $R_b$ or represents an alkyl or alkoxyalkyl radical, at least one of $R_a$, $R_b$ and $R_c$ being a substituted or unsubstituted phenyl radical, and the symbol n represents an integer from 0 to 2.

It is understood that the abovementioned alkyl radicals contain 1 to 4 carbon atoms in a linear or branched chain.

The products of general formula (I) possess various stereoisomeric forms; it is understood that the thiopyranopyrrole derivatives of the (4aR,7aR) form or of the (4aS, 7aS) form in a pure state, or in the form of a mixture of the cis- (4aRS,7aRS) forms are included within the scope of the present invention.

Furthermore, the products of general formula (I) for which n=1 also have axial or equatorial stereoisomers at the level of the S-oxide. It is understood that the position-1 R and S derivatives and mixtures thereof are also included within the scope of the present invention.

According to the invention, the thiopyranopyrrole derivative of general formula (I) may be obtained by treating the derivative of general formula:

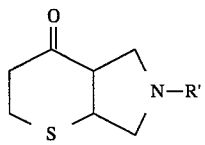

in which R' is defined as R except for representing a hydrogen atom, successively with a phenylmagnesium halide, and then with benzene in the presence of zirconium tetrachloride, followed optionally by removal of the protective radical R'0 if it is desired to obtain a product for which R is a hydrogen atom, and/or followed, where appropriate, by oxidation of the product obtained, in order to obtain a thiopyranopyrrole derivative for which n=1 or 2.

The treatment of the thiopyranopyrrole derivative of general formula (II) is carried out according to the usual methods. The treatment with a phenylmagnesium halide is advantageously carried out using phenylmagnesium bromide in an ether (for example ethyl ether), at a temperature between 20° C. and the reflux temperature of the reaction mixture. The treatment with benzene in the presence of zirconium tetrachloride is carried out at a temperature of between 20° C. and the reflux temperature of the reaction mixture.

Where appropriate, when it is desired to remove the radical R', the procedure is carried out using any known method which does not affect the rest of the molecule.

In particular, when R' is other than an allyl radical, the group R' may be removed by catalytic hydrogenation in the presence of palladium. Generally, the reaction is carried out in an acidic medium in a solvent such as an alcohol (methanol, ethanol), in water or directly in acetic acid or formic acid, at a temperature between 20° and 60° C.

When R' is a benzhydryl or trityl radical, the removal may be carried out by treatment in an acidic medium, by carrying out the procedure at a temperature between 0° C. and the reflux temperature of the reaction mixture, in an alcohol, in an ether, in water or directly in acetic acid, formic acid or trifluoroacetic acid.

The group R' may also be removed by reacting vinyl chloroformate, 1-chloroethyl chloroformate or phenyl chloroformate, a product of general formula:

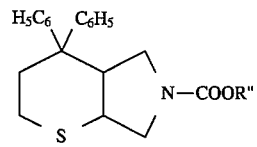

in which R" is a vinyl, 1-chloroethyl or phenyl radical, being obtained as an intermediate, and then by removing the radical R" by acid treatment. The reaction of the chloroformate is generally carried out in an organic solvent such as a chlorine-containing solvent (for example dichloromethane, dichloroethane, chloroform), an ether (for example tetrahydrofuran, dioxane) or a ketone (for example acetone) or in a mixture of these solvents, by carrying out the procedure at a temperature between 20° C. and the reflux temperature of the reaction mixture. The removal of the radical R" is carried out by treatment in an acidic medium for example with trifluoroacetic, formic, methanesulphonic, p-toluenesulphonic, hydrochloric or hydrobromic acid in a solvent such as an alcohol, an ether, an ester, a nitrile or a mixture of these solvents or in water, at a temperature between 0° C. and the reflux temperature of the reaction mixture. Under the conditions for removing the abovementioned R" radicals, the thiopyranopyrrole derivative of general formula (I) is obtained directly in the form of a salt of the acid used.

When it is desired to obtain a thiopyranopyrrole derivative of general formula (I) for which n equals 1 or 2, the oxidation reaction is carried out using any known method for the oxidation of sulphides to sulphoxides or to sulphones, which does not affect the rest of the molecule, using the product for which the amine functional group is protected. For example, the procedure is carried out by reaction of an organic peracid (percarboxylic or persulphonic acid, especially perbenzoic acid, 3-chloroperbenzoic acid, 4-nitroperbenzoic acid, peracetic acid, pertrifluoroacetic acid, performic acid, permaleic acid, monoperphthalic acid, percamphoric or pertoluenesulphonic acid) or inorganic peracids (for example periodic or persulphuric acid). The reaction is advantageously carried out in a chlorine-containing solvent (methylene chloride) at a temperature between 0° and 25° C. It is also possible to carry out the procedure using tert-butylhydroperoxide in the presence of titanium tetraisopropylate.

When it is desired to obtain a product of general formula (I) for which n=2, the procedure is carried out using 2 equivalents of oxidizing agent.

When appropriate, the choice, the introduction and the removal of the amino-protecting radical is carried out according to the usual methods which do not affect the rest of the molecule; in particular, the procedure is carried out according to the methods described by T. W. Greene, Protective Groups in Organic Synthesis, A. Wiley—Interscience Publication (1981), or by Mc Omie, Protective Groups in Organic Chemistry, Plenum Press (1973).

It is also advantageous to carry out the procedure using the product of general formula (I) for which n=0 in the form of a salt with an inorganic acid (for example hydrochloride, sulphate).

In practice, it is understood that in order to prepare a product of general formula (I) for which n=1 or 2 and for which R is a hydrogen atom, it is advantageous to carry out the oxidation before the removal of the protective radical R'.

According to the invention, the thiopyranopyrrole derivative of general formula (I) for which n=2, may also be obtained from 3,4-dihydro-4,4-diphenyl-2H-thiapyran 1,1-dioxide of formula:

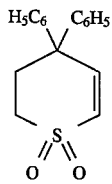
(IV)

by cycloaddition reaction with a silylated derivative of general formula:

in which R' is defined as above, $(R')_3$ represents alkyl radicals or alkyl and phenyl radicals and R" represents an alkoxy, cyano or phenylthio radical, followed optionally by the removal of the protective radical R' under the conditions described above if it is desired to obtain a derivative of general formula (I) for which R is a hydrogen atom.

The cycloaddition reaction is carried out in the presence of a catalytic amount of an acid chosen from trifluoroacetic acid, acetic acid, methanesulphonic acid or the acids given in the references mentioned below, in an organic solvent such as a chlorine-containing solvent (for example dichloromethane, dichloroethane), in an aromatic hydrocarbon, in a nitrile (acetonitrile) or in an ether, at a temperature between 0° C. and the reflux temperature of the reaction mixture.

The thiopyranopyrrole derivative of general formula (II) may be obtained by cycloaddition reaction, by reaction of a silylated derivative of general formula (V) with 4-dehydrothiapyranone of formula:

(VI)

under conditions identical to those described above for the cycloaddition reaction of this product with the sulphone of formula (IV).

The silylated derivative of general formula (V) may be obtained according to the methods described by:

Y. Terao et al., Chem. Pharm. Bull., 33, 2762 (1985);

A. Hosomi et al., Chem. Lett., 1117 (1984);

A. Padwa et al., Chem. Ber., 119, 813 (1986) or

Tetrahedron, 41, 3529 (1985).

3,4-Dihydro-4,4-diphenyl-2H-thiapyran 1,1-dioxide of formula (IV) may be obtained by successive oxidation of 3,4-dihydro-4,4-diphenyl-2H-thiapyran and of 3,4-dihydro-4,4-diphenyl-2H-thiapyran 1-oxide of formulae:

(VII)

(VIII)

The oxidation reaction is carried out under the conditions described above for the preparation of the products of general formula (I). It is not essential to isolate the S-oxide of general formula (VIII) in order to oxidize it to a sulphone.

3,4-Dihydro-4,4-diphenyl-2H-thiapyran of general formula (VII) may be prepared according to or by analogy with the method described in Example 5 below.

It is understood that the thiopyranopyrrole derivatives of general formula (I), (II) and (III) have a number of stereoisomeric forms. The separation of the (4aR, 7aR) or (4aS, 7aS) stereoisomers is advantageously carried out with respect to the derivative of general formula (I).

The separation of the stereoisomers is carried out according to any known method which is compatible with the molecule. By way of example, the separation may be carried out by the preparation of an optically active salt, by reaction of L(+)- or D(−)-mandelic acid or of dibenzoyl tartaric acid followed by separation of the isomers by crystallization. The desired isomer is released from its salt in a basic medium.

The separation of the axial and equatorial isomers may be carried out by chromatography or crystallization.

According to the invention, the new thiopyranopyrrole derivatives of general formula (I) are useful for the preparation of the derivatives which antagonise the effects of substance P and which are of the general formula:

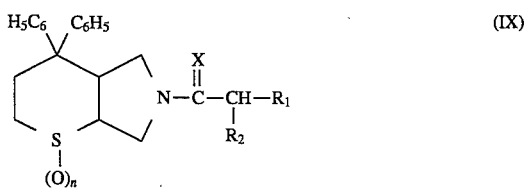

in which:

n is defined as above, the symbol X represents an oxygen atom or an NH radical, the symbol $R_1$ represents a phenyl radical which is optionally substituted by one or more halogen atoms or hydroxyl or alkyl radicals which may be optionally substituted (by halogen atoms or amino, alkylamino or dialkylamino radicals) alkoxy or alkylthio radicals which may be optionally substituted [by hydroxyl, amino, alkylamino or dialkylamino radicals optionally substituted (by phenyl, hydroxyl or amino radicals), or by dialkylamino radicals whose alkyl parts form with the nitrogen atom to which they are attached, a heterocycle with 5 to 6 members which may contain another heteroatom chosen from oxygen, sulphur or nitrogen, optionally substituted (by an alkyl, hydroxyl or hydroxyalkyl radical)], or which is substituted by amino, alkylamino or dialkylamino radicals whose alkyl parts may form with the nitrogen atom to which they are attached, a heterocycle such as defined above, or represents a cyclohexadienyl, naphthyl or a saturated or unsaturated, mono- or polycyclic heterocyclic radical containing 5 to 9 carbon atoms and one or more heteroatoms chosen from oxygen, nitrogen or sulphur, and the symbol $R_2$ represents a hydrogen or halogen atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxycarbonylamino radical, the abovementioned alkyl or acyl radicals containing 1 to 4 carbon atoms in a linear or branched chain.

In the above general formula (IX), when $R_1$ contains a halogen atom, the latter may be chosen from chlorine, bromine, fluorine or iodine;

when $R_1$ represents a saturated or unsaturated, mono-or polycyclic heterocyclic radical, it may for example be chosen from thienyl, furyl, pyridyl, dithiinyl, indolyl, isoindolyl, thiazolyl, isothiazolyl, oxazolyl, imidazolyl, pyrrolyl, triazolyl, thiadiazolyl, quinolyl, isoquinolyl or naphthyridinyl;

when $R_1$ represents a phenyl which is substituted by a chain carrying a heterocycle, the latter may be chosen from pyrrolidinyl, morpholino, piperidinyl, tetrahydropyridinyl, piperazinyl or thiomorpholino; furthermore, when the symbol $R_2$ is other than a hydrogen atom, the substituted chain on the thiopyranopyrrole has a chiral centre, it is understood that the stereoisomeric forms and mixtures thereof are also included-within the scope of the general formula (IX).

The thiopyranopyrrole derivatives of general formula (IX) may be obtained by reaction of the acid of general formula:

or of a reactive derivative of this acid, in which $R_1$ and $R_2$ are defined as above, with a thiopyranopyrrole derivative of general formula (I) for which R is a hydrogen atom and n is defined as above, followed, where appropriate, by conversion of the amide obtained to an amidine for which X represents an NH radical.

It is understood that the amino, alkylamino or carboxyl radicals contained in $R_1$ and/or $R_2$ are preferably protected beforehand.

The protection is carried out using any compatible group whose introduction and removal does not affect the rest of the molecule. In particular, according to the above mentioned methods.

By way of example, the amino or alkylamino groups may be protected with the following radicals: methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl, acetyl, benzyloxycarbonyl or its substituted derivatives;

the acidic groups may be protected with the following radicals: methyl, ethyl, t-butyl, benzyl, substituted benzyl or benzhydryl.

Furthermore, when $R_2$ represents a hydroxyl radical, it is preferable to protect this radical beforehand. The protection is carried out for example using an acetoxy, trialkylsilyl or benzyl radical or in the form of a carbonate using a —COORa radical in which Ra is an alkyl or benzyl radical. When the condensation of a reactive derivative of the acid of general formula (X) is carried out, the procedure is advantageously carried out using the acid chloride, the anhydride or a mixed anhydride or a reactive ester in which the ester residue is for example a succinimido, 1-benzotriazolyl, 4-nitrophenyl, 2,4-dinitrophenyl, pentachlorophenyl or phthalimido radical or a derivative.

The reaction is generally carried out at a temperature between −40° and +40° C., in an organic solvent such as a chlorine-containing solvent (for example dichloromethane, dichloroethane, chloroform), an ether (for example tetrahydrofuran, dioxane), an ester (for example ethyl acetate), an amide (for example dimethylacetamide, dimethylformamide), or a ketone (for example acetone) or in a mixture of these solvents, in the presence of an acid acceptor such as a nitrogen-containing organic base such as for example pyridine, dimethylaminopyridine, N-methylmorpholine or a trialkylamine (especially triethylamine) or such as an epoxide (for example propylene oxide). It is also possible to carry out the procedure in the presence of a condensation agent such as a carbodiimide, [for example dicyclohexylcarbodiimide or 1-(3-dimethylaminopropyl)-3-ethylcarbodiimide], N,N'-carbonyldiimidazole or 2-ethoxy-1-ethoxycarbonyl1,2-dihydroquinoline or alternatively in a dilute organic medium, in the presence of an alkaline condensation agent such as sodium bicarbonate, and where appropriate, the amide obtained is then converted to an amidine as defined above.

The conversion of the amide of general formula (IX) to an amidine for which X is an NH radical, is carried out by preparing the derivative of general formula:

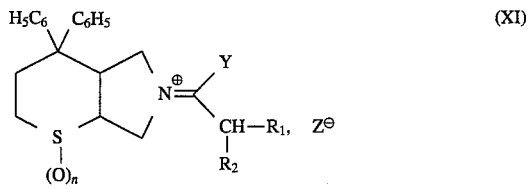

in which $R_1$, $R_2$ and n are as defined above, Y represents a chlorine atom, a methoxy or ethoxy radical and $Z^-$ represents a chloride, tetrafluoroborate, fluorosulphonate, trifluoromethylsulphonate, methyl sulphate or ethyl sulphate ion and subsequently by reacting ammonia with the derivative of general formula (XI).

The preparation of the derivative of general formula (XI) in which Y is a chlorine atom or a methoxy or ethoxy radical is carried out by reaction of a reagent such as phosgene, phosphorus oxychloride, phosphorus pentachloride, thionyl chloride, oxalyl chloride, trichloromethyl chloroformate, triethyl- or trimethyloxonium tetrafluoroborate, methyl or ethyl triflate, methyl or ethyl fluorosulphonate or methyl or ethyl sulphate. The reaction is carried out in a chlorine-containing solvent (for example dichloromethane, dichloroethane) or in an aromatic hydrocarbon (for example toluene), at a temperature between 0° C. and the reflux temperature of the reaction mixture. The reaction of ammonia with the derivative of general formula (XI) is carried out in an anhydrous organic solvent such as a chlorine-containing solvent (for example dichloromethane, dichloroethane), in an alcohol-chlorine-containing solvent mixture, in an ether (for example tetrahydrofuran), in an ester (for example ethyl acetate), in an aromatic solvent (for example toluene) or in a mixture of these solvents, at a temperature between -20° C. and the reflux temperature of the reaction mixture.

It is not essential to isolate the derivative of general formula (XI) in order to use it in this reaction.

The acids of general formula (X) may be prepared according to the methods described in the examples below, or by analogy with these methods.

The thiopyranopyrrole derivatives of general formula (IX) for which X is an NH radical, may also be obtained from the thiopyranopyrrole derivative of general formula (I) for which R is a hydrogen atom, by reaction of a product of general formula:

optionally in the form of a salt, in which $R_1$ and $R_2$ are as defined above and $R_3$ represents an alkoxy radical containing 1 to 4 carbon atoms in a linear or branched chain, or a methylthio, ethylthio, benzylthio or alkoxycarbonylmethylthio radical.

The reaction is carried out using the derivative of general formula (XII), which is optionally prepared in situ, in an organic solvent such as a chlorine-containing solvent (for example dichloromethane, dichloroethane), an ether (for example tetrahydrofuran), an aromatic hydrocarbon (for example toluene) or a nitrile for example acetonitrile, at a temperature between 0° C. and the reflux temperature of the reaction mixture.

It is understood that should the radicals $R_1$ and/or $R_2$ of the product of general formula (XII) carry substituents which may interfere with the reaction, these substituents should be protected beforehand.

The new thiopyranopyrrole derivatives of general formula (I) and the derivatives of general formula (IX) which they produce, may be purified, where appropriate, by physical methods such as crystallization or chromatography.

Where appropriate, the new derivatives of general formula (I) or the derivatives of general formula (IX) for which the symbols $R_1$ and/or $R_2$ contain amino or alkylamino substituents and/or X represents an NH radical, may be converted to the addition salts with acids. The salts formed with inorganic acids (hydrochlorides, hydrobromides, sulphates, nitrates, phosphates) or with organic acids (succinates, fumarates, tartrates, acetates, propionates, maleates, citrates, methanesulphonates, p-toluenesulphonates, isethionates or with substituted derivatives of these compounds) may be mentioned as examples of addition salts with acids.

Substance P is known to be involved in a certain number of pathological domains:

Agonists and Antagonists of Substance P, A. S. Dutta Drugs of the Future, 12 (8), 782 (1987);

Substance P and Pain: an updating, J. L. Henry, TINS, 3 (4), 97 (1980);

Substance P in Inflammatory Reactions and Pain, S. Rosell, Actual. Chim. Ther., 12th series, 249 (1985);

Effects of Neuropeptides on Production of Inflammatory Cytokines by Human Monocytes, M. Lotz et al., Science, 241, 1218 (1988);

Neuropeptides and the Pathogenesis of Allergy, Allergy, 42, 1 to 11 (1987);

Substance P in Human Essential Hypertension, J. Cardiocascular Pharmacology, 10 (suppl. 12), 5172 (1987).

The thiopyranopyrrole derivatives of general formula (IX) which antagonise the effects of substance P may find an application in the domains of analgesia, inflammation, asthma, allergies, on the central nervous system, on the cardiovascular system, as an antispasmodic, or on the immune system as well as in the domain of the stimulation of lachrymal secretions.

Indeed, these products exhibit an affinity for substance P receptors at doses of between 10 and 2000 nM according to the technique described by C. M. Lee et al., Mol. Pharmacol., 23., 563–69 (1983).

Furthermore, it has been demonstrated, using various products, that it is a substance P-antagonising effect. In the technique described by S. Rosell et al., Substance P, Ed. by US Von Euler and B. Pernow, Raven Press, New York (1977), pages 83 to 88, the products studied proved to be active at doses of between 20 and 2000 nM.

Moreover, the thiopyranopyrrole derivatives according to the present invention are not toxic, they proved nontoxic in mice by the subcutaneous route at a dose of 40 mg/kg or by the oral route at a dose of 100 mg/kg.

The following products are of particular interest:

4,4-diphenylperhydrothiopyrano[2,3-c]pyrrole;

4,4-diphenylperhydrothiopyrano[2,3-c]pyrrole 1-oxide;

4,4-diphenylperhydrothiopyrano[2,3-c]pyrrole 1,1-dioxide;

4,4-diphenyl-6-vinyloxycarbonylperhydrothiopyrano[2,3-c]pyrrole;

4,4-diphenyl-6-tert-butyloxycarbonylperhydrothiopyrano[2,3-c]pyrrole 1-oxide;

as well as their salts, their stereoisomeric forms and mixtures thereof.

EXAMPLES

The following examples, given with no limitation being implied, illustrate the present invention.

In the following examples, it is understood, unless specifically stated, that the proton NMR spectra were established at 250 MHz in dimethyl sulphoxide; the chemical shifts are expressed in ppm.

Example 1

4.35 g of (4aRS,7aRS)-4,4-diphenyl-6-vinyl- oxycarbonyl-perhydrothiopyrano[2,3-c]pyrrole are treated with 30 cm$^3$ of a 5.7N solution of hydrochloric acid in dry dioxane for 30 minutes at 20° C. The solution is concentrated to dryness under reduced pressure (2.7 kPa), the residue is taken up in 150 cm$^3$ of ethanol, the resulting solution is refluxed for 30 minutes and it is then concentrated to dryness. The solid obtained is washed with 50 cm$^3$ of ethyl ether, drained and dried. 3.64 g of (4aRS,7aRS)-4,4-diphenylperhydrothiopyrano[2,3-c]pyrrole hydrochloride are obtained in the form of a white solid.

Infrared spectrum (KBr, characteristic bands cm$^{-1}$): 3060, 3030, 3000, 2250, 1600, 1495, 1580, 1450, 755, 710, 700.

Proton NMR spectrum ( DMSO-d$_6$, main signals ): 2.2 to 2.9 (mt, 4H, CH$_2$ at 2 and CH$_2$ at 3 ); 2.4 and 3.3 ( 2mt, 2H, CH$_2$ at 5); 3.08 (d, J=12.5, 1H, 1H at 7); 3.7 (mt, 1H, H at 4a); 4.16 (t, J=5, 1H, H at 7a); 7.1 to 7.5 (mt, 10H, aromatics).

(4aRS,7aRS)-4,4-Diphenyl-6-vinyloxycarbonylperhydrothiopyrano[2,3-c]pyrrole may be prepared in the following manner:

1.72 cm$^3$ of vinyl chloroformate are added to 6.2 g of (4aRS,7aRS)-6-benzyl-4,4-diphenylperhydrothio-pyrano-[2,3-c]pyrrole in 50 cm$^3$ of 1,2-dichloroethane. The mixture is refluxed for 15 minutes and then concentrated to dryness under reduced pressure (2.7 kPa). The residue is chromatographed on a silica gel column (0.04 mm–0.06 mm, diameter 25 cm), eluting under a nitrogen pressure of 0.6 bar, with a cyclohexane and ethyl acetate mixture (90/10 by volume) and collecting fractions of 60 cm$^3$. Fractions 5 to 16 are pooled and concentrated to dryness under reduced pressure (2.7 kPa), the residue is triturated in 70 cm$^3$ of diisopropyl oxide, the suspension is filtered and the solid drained and dried. 4.35 g of (4aRS,7aRS)4,4-diphenyl-6-vinyloxycarbonylperhydrothiopyrano[2,3-c]pyrrole are obtained in the form of a white solid; melting point 160° C.

(4aRS,7aRS)-6-Benzyl-4,4-diphenylperhydrothiopyrano[2,3-c]pyrrole may be prepared in the following manner:

43.7 g of zirconium tetrachloride are added to a solution of 12.2 g of (4RS,4aSR,7aRS)-4-hydroxy4-phenyl-6-benzylperhydrothiopyrano[2,3-c]pyrrole in 180 cm$^3$ of benzene. The reaction mixture is refluxed for 1 hour and then brought to 20° C. and diluted with 200 cm$^3$ of dichloromethane. 150 cm$^3$ of a 4N aqueous solution of sodium hydroxide are added to the resulting cooled solution. The suspension obtained is filtered, the filtrate is decanted, the organic phase is washed with 200 cm$^3$ of a saturated aqueous solution of sodium chloride, dried over magnesium sulphate and concentrated to dryness under reduced pressure (2.7 kPa). The oil obtained is chromatographed on a silica gel column (0.04 mm–0.06 mm, diameter 5.2 cm, height 39 cm), eluting under a nitrogen pressure of 0.6 bar, with a cyclohexane and ethyl acetate mixture (90/10 by volume) and collecting fractions of 125 cm$^3$. Fractions 19 to 32 are pooled and concentrated to dryness under reduced pressure (2.7 kPa). The oil obtained is crystallized from 200 cm$^3$ of diisopropyl oxide, the crystals are drained and dried. 6.2 g of (4aRS,7aRS)-6-benzyl-4,4-diphenylperhydrothiopyrano[2,3-c]pyrrole are obtained in the form of orange-colored crystals; melting point 130° C.

(e4RS,4aSR,7aRS)-4-Hydroxy-4-phenyl-6-benzyl- perhydrothiopyrano[2,3-c]pyrrole may be prepared in the following manner:

A solution of 21.15 g of (4aRS,7aSR)6-benzyl-4-oxoperhydrothiopyrano[2,3-c]pyrrole in 150 cm$^3$ of anhydrous ethyl ether are added over 30 minutes to a solution of phenylmagnesium bromide prepared from 19.8 cm$^3$ of bromobenzene and 4.52 g of dry magnesium in 120 cm$^3$ of anhydrous ethyl ether. The reaction mixture is stirred at the reflux temperature for 3 hours, and then for 20 hours at 20° C. The mixture, to which 200 cm$^3$ of ethyl ether has been added, is stirred with 600 cm$^3$ of a saturated aqueous solution of ammonium chloride. The aqueous phase is extracted with 200 cm$^3$ of ethyl ether, the two pooled etherial extracts are washed twice with 300 cm$^3$ of a saturated aqueous solution of sodium chloride and then dried over magnesium sulphate and concentrated to dryness under reduced pressure (5.4 kPa) at 35° C. 12.2 g of (4RS,4aSR,7aRS)-4-hydroxy-4-phenyl6-benzylperhydrothiopyrano[2,3-c]pyrrole are obtained in the form of a white solid; melting point 137° C.

(4aRS,7aSR)-6-Benzyl-4-oxoperhydrothiopyrano[2,3-c]pyrrole may be prepared in the following manner:

5 drops of trifluoroacetic acid are added to a solution of 20 g of 4-dehydrothiapyranone and 54 cm$^3$ of N-butoxymethyl-N-trimethylsilylmethylbenzylamine in 100 cm$^3$ of anhydrous dichloromethane, and the mixture is stirred for 4 hours while maintaining the temperature at 20° C. The reaction mixture is stirred with 5 g of potassium carbonate, filtered and then concentrated to dryness under reduced pressure (2.7 kPa). The oily residue is chromatographed on a silica gel column (0.04 mm–0.06 mm, diameter 9.2 cm), eluting under a nitrogen pressure of 0.6 bar with a cyclohexane and ethyl acetate mixture (90/10 by volume) and then with the cyclohexane and ethyl acetate mixture (75/25 by volume) and collecting fractions of 250 cm$^3$. Fractions 35 to 56 are pooled and concentrated to dryness under reduced pressure (2.7 kPa). 24 g of (4aRS,7aSR)6-benzyl-4-oxoperhydrothiopyrano[2,3-c]pyrrole are obtained in the form of a yellow oil.

Infrared spectrum (CCl$_4$ solution, characteristic bands cm$^-$): 3090, 3070, 3025, 2925, 2850, 2800, 2730, 1710, 1600, 1585, 1495, 1475, 1450, 700.

Proton NMR spectrum (CDCl$_3$, main signals): 2.42 (dd, J=10 and 7, 1H, 1H at 7); 2.66 (mt, 2H, CH$_2$ at 5); 3.05 (mt, 1H, H at 4a); 3.1 (dd, J=10 and 7.5, 1H from CH$_2$ at 7); 3.61 (s, 2H, N—CH$_2$—Ar); 3.8 (dt, J=7.5 and 7, 1H, H at 7a); 7.15 to 7.35 (mt, 5H aromatics).

Example 2

3.98 g of 4,4-diphenyl-6-tert-butyloxycarbonylbutyloxycarbonylperhydrothiopyrano[2,3-c]pyrrole 1-oxide (mixture of the 1RS,4aSR,7aSR and 1RS,4aRS,7aRS isomers) are treated with 40 cm$^3$ of a mixture of concentrated hydrochloric acid (37% hydrochloric acid) and dioxane (1/2 by volume) for 48 hours at 20° C. The solution is concentrated to dryness at 40° C. under reduced pressure (2.7 kPa). The oil obtained is taken up in 30 cm$^3$ of dichloromethane, the solution is washed with 60 cm$^3$ of a 2N aqueous solution of sodium hydroxide, the aqueous phase is extracted with 20 cm³ of dichloromethane. The organic extracts are pooled, dried over magnesium sulphate and concentrated to dryness at 40° C. under reduced pressure (2.7 kPa). The residue is taken up in diisopropyl oxide and then concentrated to dryness at 40° C. under reduced pressure (2.7 and then 0.13 kPa). 3.0 g of (1RS,4aRS,7aRS)-4,4-diphenylperhydrothiopyrano[2,3-c]pyrrole 1-oxide are obtained in the form of a white meringue.

Infrared spectrum (KBr, characteristic bands cm⁻¹): 3080, 3055, 3025, 2950, 2920, 2880, 2860, 1595, 1580, 1490, 1440, 1020, 760, 740, 700.

Proton NMR spectrum (DMSO-$d_6$+CF$_3$CCOD, main signals): 2.26 (broad t, J=14, 1H, 1H at 3); 2.42 (dd, J=10 and 9, 1H, CH$_2$ at 5); 2.55 (broad dd, J=14 and 4, 1H, 1H at 3); 3.68 (t, J=6, 1H, H at 7a); 3.82 (d, J=14, 1H, H at 7); 3.8 to 4 (mt, 1H, CH at 4a); 4.15 (dd, J=14 and 6, 1H, H at 7); 7.1 to 7.5 (mt, 10H aromatics).

4,4-Diphenyl-6-tert-butyloxycarbonylperhydrothiopyrano[2,3-c]pyrrole 1-oxide (mixture of the 1RS,4aSR, 7aSR and 1RS,4aRS,7aRS isomers) may be prepared in the following manner:

A solution of 2.3 g of 3-chloroperoxybenzoic acid (at 85%) in 20 cm³ of dichloromethane is added to a solution, cooled to 0° C., of 4.2 g of (4aRS,7aRS)4,4-diphenyl-6-tert-butyloxycarbonylperhydrothiopyrano[2,3-c]pyrrole in 30 cm³ of dry dichloromethane. After stirring for 1.5 hours at 3° C. and 1.5 hours at 20° C., the reaction mixture is washed twice with 100 cm³ of a saturated aqueous solution of sodium bicarbonate, and then with 100 cm³ of distilled water, dried over magnesium sulphate, concentrated to dryness at 35° C. under reduced pressure (2.7 kPa). The residue is crystallized from ethyl acetate, the crystals are washed with ethyl acetate and diisopropyl oxide, drained and then dried under reduced pressure (2.7 kPa). 3.98 g of 4,4-diphenyl-6-tert-butyloxycarbonylperhydrothiopyrano[2,3-c]pyrrole 1-oxide—(mixture of the 1RS,4aSR,7aSR and 1RS,4aRS,7aRS isomers) are obtained in the form of white crystals used as they are in the next reaction.

(4aRS,7aRS)-4,4-Diphenyl-6-tert-butyloxycarbonylperhydrothiopyrano[2,3-c]pyrrole may be prepared in the following manner:

2.89 g of ditert-butyl dicarbonate are added in fractions of 0.5 g to a suspension of 4.0 g of (4aRS,7aRS)-4,4-diphenylperhydrothiopyrano[2,3-c]pyrrole hydrochloride and 1.70 cm³ of triethylamine in 60 cm³ of dry dichloromethane, followed by 0.15 g of 4-dimethylaminopyridine. The mixture is stirred for 20 hours at 20° C. and then the reaction solution is washed twice with 100 cm³ of an aqueous solution of citric acid of pH 4 and with 100 cm³ of water, dried over magnesium sulphate and concentrated to dryness at 35° C. under reduced pressure (2.7 kPa). The residue is crystallized from ethyl ether, the crystals are drained and dried. 4.27 g of (4aRS,7aRS)-4,4-diphenyl-6-tert-butyloxycarbonylperhydrothiopyrano[2,3-c]pyrrole are obtained in the form of pink crystals; melting point 162° C.

(1RS,4aRS,7aRS)-4,4-Diphenylperhydrothiopyrano[2,3-c]pyrrole 1-oxide may also be prepared in the following manner:

A solution of 15.4 g of 3-chloroperoxybenzoic acid (at 85%) in 400 cm³ of dichloromethane is added over 40 minutes to a solution, cooled to −3° C., of 25 g of (4aRS,7aRS)-4,4-diphenylperhydrothiopyrano[2,3-c]pyrrole in 500 cm³ of dichloromethane and 100 cm³ of methanol. After stirring for one hour at −3° C., the reaction mixture is washed with 200 cm³ of a 10% aqueous solution of potassium hydrogen carbonate and again with 100 cm³ of this same solution, then dried over magnesium sulphate and concentrated to dryness at 40° C. under reduced pressure (2.7 kPa). The residue is crystallized from 50 cm³ of ethyl acetate, the crystals are taken up in 200 cm³ of dichloromethane, the solution obtained is washed with 75 cm³ of a 1N aqueous solution of sodium hydroxide and then dried over magnesium sulphate and concentrated to dryness. The residue is crystallized from 30 cm³ of ethyl acetate, the crystals are washed with ethyl acetate, drained and dried. 13.6 g of (1RS,4aRS,7aRS)-4,4-diphenylperhydrothiopyrano[ 2,3-c]-pyrrole 1-oxide are obtained in the form of white crystals; melting point 174° C.

Example 3

3.5 g of (S)-mandelic acid and 90 cm³ of a mixture of acetonitrile and water (99/1 by volume) are added to 7.15 g of (1RS,4aRS,7aRS)-4,4-diphenylperhydrothiopyrano[2,3-c]pyrrole 1-oxide. After stirring, the resulting solution is allowed to stand for 48 hours at room temperature. The crystals obtained are drained, washed with the acetonitrile-water mixture and then dried. The crystals are taken up in 200 cm³ of a boiling acetonitrile-water mixture and after filtering while still hot, the solution obtained is allowed to stand for 5 hours at room temperature. The crystals are drained, washed twice with 10 cm³ of acetonitrile and then dried. 1.5 g of (1R*,4aR*,7aR*)4,4-diphenylperhydrothiopyrano[2,3-c]pyrrole 1-oxide (S)-mandelate are obtained; $[\alpha]_D^{20}$=−228°, (c =0 44; acetic acid). The filtrate is allowed to stand for 20 hours at room temperature, the crystals obtained are drained, washed twice with 5 cm³ of acetonitrile and then dried. 0.62 g of (1R*,4aR*,7aR*)-4,4-diphenylperhydrothiopyrano[2,3-c]pyrrole 1-oxide (S)-mandelate is obtained; $[\alpha]_D^{20}$=−230°, (c =0.45; acetic acid).

40 cm³ of dichloromethane and 7.0 cm³ of 1N aqueous sodium hydroxide are added to 2.06 g of (1R*,4aR*,7aR*)-4,4-diphenylperhydrothiopyrano[2,3-c]pyrrole 1-oxide (S)-mandelate. The mixture is stirred for a few minutes after dissolution of the starting product, the organic phase is dried over magnesium sulphate and concentrated to dryness under reduced pressure (2.7 kPa). The residue is disintegrated in an ethyl acetate and ethyl ether mixture, the solid is washed with diisopropyl oxide and dried. 1.14 g of (1R*,4aR*, 7aR*)-(-)-4,4-diphenylperhydrothiopyrano-[2,3-c]pyrrole 1-oxide are obtained in the form of a white solid; melting point 192° C. $[\alpha]_D^{20}$=−405°, (c=0.46; acetic acid).

Example 4

15.8 g of (S)-(+)-mandelic acid and 750 cm³ of a mixture of acetonitrile and water (99/1 by volume) are added to 32.3 g of (1RS,4aRS,7aRS)-4,4-diphenylperhydrothiopyrano[2, 3-c]pyrrole 1-oxide, followed by 5.0 cm³ of water. After making lukewarm, the solution obtained is allowed to stand for 48 hours at room temperature. The crystalline suspension is filtered, and the filtrate, concentrated to dryness, gives a meringue which is taken up in 200 cm³ of the boiling acetonitrile-water mixture. The solution obtained is allowed to stand for about 20 hours at room temperature. The crystals are drained, washed with acetonitrile, dried and then again taken up in 200 cm³ of an acetonitrile-water mixture (98/2 by volume). The resulting solution is allowed to stand for about 20 hours at room temperature. The crystals are drained and dried. 9.4 g of (1R*,4aR*,7aR*)-4,4-diphenylperhydrothiopyrano[2,3-c]pyrrole 1-oxide (S)-(+)-mandelate are obtained; $[\alpha]_D^{20}$=+337°(c=0 45; acetic acid)

100 cm³ of dichloromethane and 30 cm³ of 1N aqueous sodium hydroxide are added to 9.2 g of (1R*,4aR*,7aR*)-4,4-diphenylperhydrothiopyrano[2,3-c]pyrrole 1-oxide (S)-(+)-mandelate. The mixture is stirred for 10 minutes, the organic phase is dried over magnesium sulphate, and concentrated to dryness under reduced pressure (2.7 kPa). The residue is disintegrated in an ethyl acetate and diisopropyl oxide mixture, the solid is washed with diisopropyl oxide and dried. 5.6 g of (1R*,4aR*,7aR*)-(+)-4,4-diphenylperhydrothiopyrano[2,3-c]pyrrole 1-oxide are obtained in the form of a white solid; melting point 198° C. $[\alpha]_D^{20}$ +434°, (c =0 45; acetic acid).

Example 5

0.58 g of (4aRS,7aRS)-4,4-diphenyl-6-vinyloxycarbonyl perhydrothiopyrano[2,3-c]pyrrole 1,1-dioxide is treated with 25 cm³ of a 5.7N solution of hydrochloric acid in dry dioxane for 30 minutes while making lukewarm. The reaction solution is concentrated to dryness under reduced pressure (2.7 kPa) at 50° C. The residue is taken up in 15 cm³ of ethanol, the solution obtained is refluxed for 30 minutes and then concentrated to dryness. The solid obtained is washed with ethyl ether, drained and dried. 0.46 g of (4aRS,7aRS)-4,4-diphenylperhydrothiopyrano[2,3-c] pyrrole 1,1-dioxide hydrochloride is obtained in the form of a white solid.

Infrared spectrum (characteristic bands cm⁻): 3055, 3030, 2970, 2935, 2825, 2300, 1600, 1495, 1462, 1335, 1315, 1300, 1140, 1120, 770, 760, 710, 595, 505.

Proton NMR spectrum (DMSO-$d_6$ +CF₃COOD, main signals): 3.84 (ab, 2H, CH₂ at 7); 4.0 (mt, 1H, H at 4a); 4.27 (mt, 1H, H at 7a); 7.1 to 7.6 (mt, 10H, aromatics).

(4aRS,7aRS)-4,4-Diphenyl-6-vinyloxycarbonylperhydrothiothiopyrano[2,3-c]pyrrole 1,1-dioxide may be prepared in the following manner:

0.16 cm³ of vinyl chloroformate is added to a solution of 0.7 g of (4aRS,7aRS)-6-benzyl-4,4-diphenylperhydrothiopyrano[2,3-c]pyrrole 1,1-dioxide in 10 cm³ of 1,2-dichloroethane. The mixture is refluxed for 2 hours and then concentrated to dryness under reduced pressure (2.7 kPa) at 50° C. The crystalline solid is washed with ethyl ether, drained and then dried. 0.58 g of (4aRS,7aRS)-4,4-diphenyl-6-vinyloxycarbonylperhydrothiopyrano[2,3-c]pyrrole 1,1-dioxide is obtained in the form of white crystals.

Infrared spectrum (characteristic bands cm⁻¹): 3080, 3055, 3025, 2990, 2970, 2925, 2885, 1715, 1645, 1595, 1580, 1495, 1415, 1330, 1300, 1150, 1140, 1125, 945, 865, 755, 700, 510.

Proton NMR spectrum (DMSO-$d_6$+CF₃COOD, main signals): 2.5 to 3.45 (mt, 6H, CH₂ at 5, at 2 and at 3); 3.8 to 4.2 (mt, 4H, CH₂ at 7, H at 4a and H at 7a); 4.46 and 4.72 (broad 2d, J=6 and J=14, 2x1H, CH=CH₂); 7.0 (dd, J=14 and 6, 1H, OCH=); 7.1 to 7.6 (mt, 10H, aromatics).

(4aRS,7aRS)-6-Benzyl-4,4-diphenylperhydrothiopyrano [2,3-c]pyrrole 1,1-dioxide may be prepared in the following manner:

2 drops of trifluoroacetic acid are added to a solution of 1.3 g of 3,4-dihydro-4,4-diphenyl-2H-thiapyran 1,1-dioxide and 1.75 cm³ of N-butoxymethyl-N- trimethylsilylmethylbenzylamine in 12 cm³ of anhydrous dichloromethane, and the mixture is stirred for 30 minutes at 30° C. 1.75 cm³ of N-butoxymethyl-N-trimethylsilylmethylbenzylamine and 2 drops of trifluoroacetic acid are again added and the mixture is stirred for 2 hours at 35° C. This last procedure is once again repeated and after stirring for 1 hour, 1 g of potassium carbonate is added. The suspension is filtered and the filtrate concentrated to dryness under reduced pressure (2.7 kPa). The residue is chromatographed on a silica gel column (particle size 0.04–0.06 mm, diameter 3.2 cm, height 35 cm), eluting under a nitrogen pressure of 0.5 bar with a cyclohexane and ethyl acetate mixture (80/20 by volume) and collecting fractions of 30 cm³. Fractions 20 to 28 are pooled and concentrated to dryness under reduced pressure (2.7 kPa). 0.7 g of (4aRS,7aRS)-6-benzyl4,4-diphenylperhydrothiopyrano[2,3-c]pyrrole 1,1-dioxide is obtained in the form of white crystals; melting point 186° 1 C.

3,4-Dihydro-4,4-diphenyl-2H-thiapyran 1,1-dioxide may be prepared in the following manner:

A solution of 1.12 g of 3-chloroperoxybenzoic acid (at 85%) in 25 cm³ of dry dichloromethane is added to a solution of 1.47 g of 3,4-dihydro-4,4-diphenyl-2H-thiapyran 1-oxide in 15 cm³ of dry dichloromethane. After stirring for 20 hours at 20° C. the reaction mixture is washed with 50 cm³ of a 10% aqueous solution of sodium thiosulphate and then with 50 cm³ of a saturated aqueous solution of sodium hydrogen carbonate. The organic phase is dried over magnesium sulphate and concentrated to dryness under reduced pressure (2.7 kPa). The crystalline residue is washed with ethyl ether, drained and dried under reduced pressure (2.7 kPa). 1.3 g of 3,4-dihydro-4,4-diphenyl2H-thiapyran 1,1-dioxide are obtained in the form of white crystals; melting point 166° C.

3,4-Dihydro-4,4-diphenyl-2H-thiapyran 1-oxide may be prepared in the following manner:

By carrying out the procedure as above, using 2.05 g of 3,4-dihydro-4,4-diphenyl-2H-thiapyran and 1.67 g of 3-chloroperoxybenzoic acid (at 85%), 1.9 g of 3,4-dihydro-4,4-diphenyl-2H-thiapyran 1-oxide are obtained in the form of a white solid; melting point 130° C.

3,4-Dihydro-4,4-diphenyl-2H-thiapyran may be prepared in the following manner:

3.95 cm³ of acetic anhydride are added to a suspension of 2.7 g of 4,4-diphenyltetrahydrothiapyran 1-oxide in 30 cm³ of anhydrous toluene. The mixture is refluxed for 20 hours and concentrated to dryness at 60° C. under reduced pressure (2.7 kPa and then 0.13 kPa). The oily residue is crystallized from diisopropyl oxide, the crystals are drained and dried. 2.1 g of 3,4-dihydro-4,4-diphenyl-2H-thiapyran are obtained in the form of white crystals; melting point 78° C.

4,4-Diphenyltetrahydrothiapyran 1-oxide may be prepared in the following manner:

A solution of 20.3 g of 3-chloroperoxybenzoic acid (at 85%) in 300 cm³ of dichloromethane is added over 40 minutes to a solution, cooled to 0° C., of 25.4 g of 4,4-diphenyltetrahydrothiapyran in 130 cm³ of dichloromethane. After stirring for 2 hours at 0° C., 250 cm³ of a 5% aqueous solution of potassium hydrogen carbonate are added to the mixture and it is then stirred for 15 minutes. The organic phase is again washed with 250 cm³ of a solution of potassium hydrogen carbonate and it is then dried over magnesium sulphate and concentrated to dryness (after verifying the absence of peroxides) under reduced pressure (2.7 kPa). 26.9 g of 4,4-diphenyltetrahydrothiapyran 1-oxide are obtained in the form of a white solid; melting point 122° C.

4,4-Diphenyltetrahydrothiapyran may be prepared in the following manner:

100 g of sodium sulphide nonahydrate are added to a suspension of 140.8 g of 3,3-diphenyl-1,5-bis- (methanesulphonyl-oxy)pentane in 1400 cm³ of 1-butanol. The mixture is refluxed for 2 hours and then cooled to about 20° C. and then 1000 cm³ of water, 500 cm³ of ethyl acetate and 500 cm³ of dichloromethane are added. After stirring, the organic phase is separated, washed successively with 1000 cm³ of water, 500 cm³ of 1N hydrochloric acid, 500 cm³ of a saturated aqueous solution of sodium hydrogen carbonate and 1000 cm³ of water, and then dried over magnesium sulphate and concentrated to dryness at 60° C. under reduced pressure (2.7 kPa). The residue is crystallized from ethyl acetate, the crystals are washed with diisopropyl oxide, drained and dried. 76 g of 4,4-diphenyltetrahydrothiapyran are obtained in the form of white crystals; melting point 134° C.

3,3-Diphenyl-1,5-bis(methanesulphonyloxy)pentane may be prepared in the following manner:

A solution of 62 cm³ of methanesulphonyl chloride in 100 cm³ of dichloromethane is added over 10 minutes to a solution, cooled to −20° C., of 95 g of 3,3-diphenyl-1,5-pentanediol (prepared according to P. EILBRACHT et al., Chem. Ber. 118, 825–839 (1985)) in 950 cm³ of dichloromethane and 113 cm³ of triethylamine. After stirring for 2 hours at 20° C., the reaction mixture is washed with twice 500 cm³ of water, the organic phase is dried over magnesium sulphate and concentrated to dryness under reduced pressure (2.7 kPa). The oily residue is crystallized from ethyl ether, the crystals are washed with ethyl ether, drained and dried. 140 g of 3,3-diphenyl-1,5-bis(methanesulphonyloxy)pentane are obtained in the form of white crystals; melting point 99° C.

The products according to the invention may lead to the thiopyranopyrrole derivatives of general formula (IX) by carrying out the procedure as in the following examples:

Example of Use 1

1.18 g of N,N'-carbonyldiimidazole are added to a solution of 1.16 g of 2-dimethylaminophenylacetic acid in 20 cm³ of dry dichloromethane. The mixture is stirred for 30 minutes at +5° C. and then a solution of 2.0 g of (4aRS, 7aRS)-4,4-diphenylperhydrothiopyrano[2,3-c]pyrrole hydrochloride and 1.83 cm³ of triethylamine in 20 cm³ of dichloromethane is added. The reaction mixture is stirred for 1 hour at 20° C. and is then washed twice with 50 cm³ of water and dried over magnesium sulphate. The solution is filtered and concentrated to dryness under reduced pressure (2.7 kPa). The oil obtained is chromatographed on a silica gel column (0.04 mm–0.06 mm, diameter 2.8 cm, height 26 cm), eluting under a nitrogen pressure of 0.6 bar with a cyclohexane and ethyl acetate mixture of (60/40 by volume) and collecting fractions of 60 cm³. Fractions 6 to 20 are pooled and concentrated to dryness under reduced pressure (2.7 kPa) and the residue is crystallized from an acetonitrile and diisopropyl oxide mixture. The crystals are drained and dried. 2.16 g of (4aRS,7aRS)-6-[(2-dimethylaminophenyl)acetyl]-4,4-diphenylperhydrothiopyrano[2,3-c]pyrrole are obtained in the form of a white solid; melting point 163° C.

Example of Use 2

By carrying out the procedure as in Example of Use 1, using 1.85 g of [2-(1-pyrrolidinyl)phenyl]acetic acid hydrobromide and 2.0 g of (4aRS,7aRS)4,4-diphenylperhydrothiopyrano[2,3-c]pyrrole hydrochloride, 0.90 g of (4aRS, 7aRS)6-{[2-(1-pyrrolidinyl)phenyl]acetyl}4,4-diphenylperhydrothiopyrano[2,3-c]pyrrole is obtained in the form of white crystals; melting point 166° C.

Example of Use 3

A solution of 1.15 cm³ of phenylacetyl chloride in 25 cm³ of dichloromethane is added over 5 minutes to a solution, cooled to 0° C., of 2.63 g of (4aRS,7aRS)-4,4-diphenylperhydrothiopyrano[2,3-c]pyrrole hydrochloride and 2.42 cm³ of triethylamine in 25 cm³ of dichloromethane. After stirring for one hour at 0° C. and one hour at 20° C. 20 cm³ of dichloromethane are added. The reaction mixture is washed twice with 100 cm³ of distilled water, dried over magnesium sulphate and then concentrated to dryness under reduced pressure (2.7 kPa). The oil obtained is chromatographed on a silica gel column (0.04–0.06 mm, diameter 3.5 cm, height 26 cm), eluting under a nitrogen pressure of 0.4 bar with a cyclohexane and ethyl acetate mixture (80/20 by volume) and collecting fractions of 125 cm³. Fractions 19 to 26 are pooled and concentrated to dryness under reduced pressure (2.7 kPa). 0.87 g of (4aRS,7aRS)-6-phenylacetyl-4,4-diphenylperhydrothiopyrano[2,3-c]pyrrole is obtained in the form of a white solid; melting point 210° C.

Example of Use 4

0.58 cm³ of ethyl chloroformate is added to a solution 0.92 g of 2-hydroxyphenylacetic in 30 cm³ of dry dichloromethane. After stirring for 15 minutes at 20° C. the mixture is cooled to −15° C. and 0 85 cm³ of triethylamine is added. After stirring for 2 hours at −15° C., a suspension of 2 g of (4aRS,7aRS)-4,4-diphenylperhydrothiopyrano[2, 3-c]pyrrole hydrochloride and 1.70 cm³ of triethylamine in 30 cm³ of dichloromethane is added over 20 minutes. After stirring for 20 hours at 20° C., the reaction mixture is washed with 50 cm³ of 1N hydrochloric acid and 50 cm³ of a saturated aqueous solution of sodium chloride and then dried over magnesium sulphate and concentrated to dryness under reduced pressure (2.7 kPa). The residue is crystallized from 20 cm³ of dichloromethane, the crystals are washed with diisopropyl oxide, drained and dried under reduced pressure (2.7 kPa). 1.02 g of (4aRS,7aRS)-4,4-diphenyl6-[(2-hydroxyphenyl)acetyl]perhydrothiopyrano[2,3-c]pyrrole are obtained in the form of white crystals; melting point 248° C.

Example of Use 5

1.13 g of N,N'-carbonyldiimidazole are added to a solution, cooled to 0° C., of 1.16 g of 2-methoxyphenylacetic acid in 20 cm³ of dry dichloromethane. The mixture is stirred for 40 minutes at 0° C. and then a solution of 2.15 g of (4aRS,7aRS)4,4-diphenylperhydrothiopyrano[2,3-c]pyrrole hydrochloride and 0.9 cm³ of triethylamine in 20 cm³ of dichloromethane is added. The reaction mixture is stirred for one hour at 0° C. and is then washed with a saturated aqueous solution of sodium hydrogen carbonate. The organic phase is dried over magnesium sulphate and concentrated to dryness under reduced pressure (2.7 kPa). The solid obtained is washed with 30 cm³ of ethyl ether and 30 cm³ of diisopropyl oxide and it is then dried under reduced pressure (2.7 kPa). 2.66 g of (4aRS,7aRS)-4,4-diphenyl-6-[(2-methoxyphenyl)acetyl]perhydrothiopyrano[2,3-c]pyrrole are obtained in the form of a white solid; melting point 172° C.

Example of Use 6

6-[(S)-2-(2-Methoxyphenyl)propionyl]-4,4diphenylperhydrothiopyrano[2,3-c]pyrrole - mixture of the (4aR,7aR) and (4aS,7aS) forms, may be prepared by carrying out the procedure as described in Example 5, using 0.89 g of (S)-2-(2-methoxyphenyl)propionic acid and (4aRS,7aRS)-4,4-diphenylperhydrothiopyrano[2,3-c]pyrrole hydrochloride. 1.46 g of 6-[(S)-2-(2-methoxyphenyl)propionyl]-4,4-diphenylperhydrothiopyrano[2,3-c]pyrrole—mixture of the (4aR,7aR) and (4aS,7aS) forms, are obtained in the form of a white meringue.

First form:

Infrared spectrum (characteristic bands $cm^{-1}$): 3095, 3055, 3025, 2950, 2930, 2875, 2835, 1630, 1595, 1490, 1565, 1425, 1240, 1030, 750, 700.

Proton NMR spectrum (DMSO-$d_6$+CF$_3$COOD, a mixture of the two rotamers is observed at room temperature; characteristic signals): 1.15 and 1.20 (2d, J=7.5, 3H, CH$_3$); 2.1–2.9 (mt, 5H, 2 CH$_2$ at 5 and 3+H at 4a); 3.36 and 3.8 (2s, 3H, OCH$_3$); 6.7 to 7.4 (mt, 14H, aromatics).

Second form:

Infrared spectrum (characteristic bands $cm^{-1}$): 3095, 3060, 3025, 2960, 2930, 2870, 2835, 1640, 1600, 1495, 1465, 1425, 1240, 1035, 755, 700.

Proton NMR spectrum (DMSO-$d_6$+CF$_3$COOD, a mixture of the two rotamers is observed at room temperature; characteristic signals): 1.1 and 1.18 (2d, J=7.5, 3H, CH$_3$); 2.1–2.35 (mt, 2H, CH$_2$ at 3); 2.35–3.10 (mt, 3H, CH$_2$ at 5+H at 4a); 3.6 and 3.8 (2s, 3H, OCH$_3$); 3.95 and 4.02 (mt, 1H, H at 7a); 6.7 to 7.4 (mt, 14H, aromatics).

(S)-2-(2-Methoxyphenyl)propionic acid may be obtained in the following manner:

(S)-2-(2-Methoxyphenyl)propionic acid may be prepared by analogy with the methods described by D. A. Evans et al., Tetrahedron, 44, 5525, (1988), according to the following procedure:

1.52 g of lithium hydroxide are added to a solution, cooled to +5° C., of 4.1 g of (4S,5S)-4-methyl5-phenyl-3-[(S)-2-(2-methoxyphenyl)propionyl]2-oxazolidinone in 60 cm$^3$ of tetrahydrofuran and 30 cm$^3$ of water. The reaction mixture is stirred for 3 hours at this temperature and then, after returning to room temperature, ethyl acetate is added, the mixture decanted, the aqueous phase is acidified with a 1N aqueous solution of hydrochloric acid, extracted with ethyl acetate and the organic phase is dried over magnesium sulphate and concentrated to dryness under reduced pressure (2.7 kPa). The solid obtained is recrystallized from hexane, drained and dried. 0.4 g of (S)-2-(2-methoxyphenyl)propionic acid is obtained in the form of white crystals; melting point 102° C. $[\alpha]_D^{20}$=+84.6; (c=1; CHCl$_3$).

(4S,5S)-4-Methyl-5-phenyl-3-[(S)2-(2-methoxyphenyl)propionyl]-2-oxazolidinone may be obtained in the following manner:

19.1 g of sodium 1,1,1,3,3,3-hexamethyldisilazanate are added to a solution, cooled to –50° C., of 10 g of (4S,5S)-4-methyl-5-phenyl-3-[(2-methoxyphenyl)acetyl]-2-oxazolidinone in 150 cm$^3$ of tetrahydrofuran, the mixture is stirred for 45 minutes at this temperature and then 7.72 cm$^3$ of methyl iodide are added. The reaction mixture is then stirred for 15 hours at room temperature and then diluted with ethyl acetate, washed with 50 cm$^3$ of water and then with 50 cm$^3$ of a saturated aqueous solution of sodium chloride, dried over magnesium sulphate and concentrated to dryness under reduced pressure (2.7 kPa). The residue obtained is crystallized from isopropyl oxide, drained and dried. 4.2 g of (4S,5S)4-methyl-5-Phenyl-3-[(S)-2-(2-methoxyphenyl)propionyl]- 2-oxazolidinone are obtained in the form of a white solid.

(4S,5S)-4-Methyl-5-phenyl-3-(2-methoxyphenylacetyl)-2-oxazolidinone may be obtained in the following manner:

9.38 g of 2-methoxyphenylacetic acid are added, at room temperature, to a suspension of 1.89 g of sodium hydride (80% dispersion in vaseline) in 200 cm$^3$ of dry tetrahydrofuran. This suspension is cooled to –30° C., 7.77 cm$^3$ of pivaloyl chloride are added and then a solution, cooled to –78° C., which is obtained by adding 35.27 cm$^3$ of a 1.6M solution of butyllithium in hexane to a solution, cooled to –78° C., of 10 g of (4S,5S)-4-methyl-5-phenyl-2-oxazolidinone in 200 cm$^3$ of dry tetrahydrofuran, is finally added. The reaction mixture is stirred for 45 minutes at –30° C. and then after reequilibrating to room temperature, 200 cm$^3$ of a saturated aqueous solution of ammonium chloride is added followed by 500 cm$^3$ of ethyl acetate; after decantation, the organic phase is washed twice with 100 cm$^3$ of water and then twice with 100 cm$^3$ of a saturated aqueous solution of sodium chloride, dried over magnesium sulphate and concentrated to dryness under reduced pressure (2.7 kPa). The residue is chromatographed on a silica gel column (particle size 0.04–0.06 mm, diameter 4.8 cm, height 36 cm), eluting under a nitrogen pressure of 0.6 bar with a cyclohexane and ethyl acetate mixture (85/15 and then 80/20 by volume) and collecting fractions of 50 cm$^3$. Fractions 14 to 31 are pooled and concentrated to dryness under reduced pressure (2.7 kPa). 13.6 g of (4S,5S)-4-methyl5-Phenyl-3-(2-methoxyphenylacetyl)-2-oxazolidinone are obtained in the form of a yellow oil.

Example of Use 7

By carrying out the procedure according to that described in Example 8 below, using 1.82 g of (1RS,4aRS,7aRS)-4,4-diphenylperhydrothiopyrano[2,3-c]- pyrrole 1-oxide and 1.39 g of [(3-dimethylamino-2-propoxy)phenyl]acetic acid, 0.3 g of (1RS,4aRS,7aRS)-6-{[(3-dimethylamino-2-propoxy)phenyl]acetyl}- 4,4-diphenylperhydrothiopyrano[2,3-c]pyrrole 1-oxide is obtained in the form of white crystals; melting point 150° C.

Example of Use 8

0.03 g of hydroxybenzotriazole hydrate is added to a solution, cooled to 0° C., of 1.06 g of ( 1R*, 4aR*, 7aR*)-(–)-4,4-diphenylperhydrothiopyrano[2,3-c]pyrrole and 0.81 g of 2-[( 3-dimethylamino-2-propoxy)phenyl]acetic acid in 60 cm$^3$ of dry dichloromethane, followed by 0.77 g of 1-(3-dimethylaminopropyl)-3-ethylcarbodiimide. After stirring for 2 hours at 0° C. and 20 hours at 20° C., the reaction mixture is washed with 20 cm$^3$ of water and then dried over magnesium sulphate and concentrated to dryness under reduced pressure (2.7 kPa). The residue is chromatographed on a silica gel column (particle size 0.04–0.06 mm, diameter 2.4 cm, height 35 cm), eluting under a nitrogen pressure of 0.6 bar with an ethyl acetate, acetic acid and water mixture (60/10/10 by volume) and collecting fractions of 50 cm$^3$. Fractions 8 to 19 are pooled and concentrated to dryness under reduced pressure (2.7 kPa). The residue is taken up in 60 cm$^3$ of dichloromethane, the solution is washed with 20 cm$^3$ of a 1N aqueous solution of sodium hydroxide, dried over magnesium sulphate and then concentrated to dryness. The solid obtained is recrystallized from an ethyl acetate and ethyl ether mixture, the crystals are washed with diisopropyl oxide, drained and dried. 0.99 g of (1R*,4aR*,7aR*)-(–)-6-{2-[(3-dimethylamino2-propoxy)phenyl]acetyl}-4,4-diphenylperhydrothiopyrano[2,3-c]pyrrole 1-oxide is obtained in the form of a white solid; melting point 120° C. $[\alpha]_D^{20}$=–323° ; (c=0.5; acetic acid).

Example of use 9

0.03 g of hydroxybenzotriazole hydrate is added to a solution, cooled to +5° C., of 0.69 g of (1RS,4aRS,7aRS)-

4,4-diphenylperhydrothiopyrano[2,3-c]pyrrole 1-oxide and 0.68 g of {[3-(1-pyrrolidinyl)-2-propoxy]phenyl}acetic acid in 25 cm³ of dry dichloromethane, followed by a solution of 0.5 g of 1-(3-dimethylaminopropyl)-3-ethylcarbodiimide hydrochloride in 20 cm³ of dry dichloromethane. After stirring for 2 hours at +5° C. and 20 hours at 20° C., the reaction mixture is washed twice with 50 cm³ of distilled water and dried over magnesium sulphate and then concentrated to dryness under reduced pressure (2.7 kPa). The residue obtained is chromatographed on a silica gel column (particle size 0.04–0.06 mm, diameter 2.4 cm, height 32 cm), eluting under a nitrogen pressure of 0.8 bar with an ethyl acetate, acetic acid and water mixture (80/20/20 by volume) and collecting fractions of 25 cm³. Fractions 21 to 50 are pooled and concentrated to dryness under reduced pressure (2.7 kPa). The residue is crystallized from 8 cm³ of ethyl acetate, the crystals are washed with ethyl acetate and diisopropyl oxide and then dried. 0.45 g of (1RS,4aRS,7aRS)-6-{{[3-(1-pyrrolidinyl)-2-propoxy]phenyl}acetyl}-4,4-diphenylperhydrothiopyrano[2,3-c]-pyrrole 1-oxide is obtained in the form of beige crystals; melting point 126° C.

Example of Use 10

0.06 g of hydroxybenzotriazole hydrate and 1.01 g of 1-( 3-dimethylaminopropyl )-3-ethylcarbodiimide hydrochloride are added to a solution, cooled to about 0° C., of 1.43 g of (1R*,4aR*,7aR*)-(–)-4,4-diphenylperhydrothiopyrano [2,3-c]pyrrole 1-oxide and 0.83 g of (S)-2-(2-methoxyphenyl)propionic acid in 100 cm³ of dry dichloromethane. After stirring for 2 hours at 0° C. and 2 hours at 20° C., the reaction mixture is washed with 50 cm³ of water and then dried over magnesium sulphate and concentrated to dryness under reduced pressure (2.7 kPa). The residue is crystallized from acetonitrile, the crystals are drained, washed several times with ethyl ether and then dried.

1.56 g of (1R*,4aR*,7aR*)-(–)-6-[(S)2-(2-methoxyphenyl)propionyl]-4,4-diphenylperhydrothiopyrano[2,3-c]pyrrole 1-oxide are obtained in the form of white crystals; melting point 170° C. $[\alpha]_D^{20} = -316°$ ; (c=0.50; acetic acid).

Example of Use 11

By carrying out the procedure as described in Example 1 above, using 0.49 g of 2-dimethylaminophenylacetic acid, 0.50 g of N,N'-carbonyldiimidazole, 0.70 cm³ of triethylamine and 1.0 g of (4aRS,7aRS)4,4-diphenylperhydrothiopyrano [2,3-c]pyrrole 1,1-dioxide hydrochloride, 0.55 g of ( 4aRS, 7aRS )6-(2-dimethylaminophenyl)-4,4-diphenylperhydrothiopyrano[ 2,3-c]pyrrole 1,1-dioxide is obtained in the form of white crystals; melting point 226° C.

Example of Use 12

0.35 cm³ of triethylamine and a solution of 0.17 cm³ of phenylacetyl chloride in 5 cm³ of dichloromethane are added to a suspension, cooled to 0° C., of 0.46 g of (4aRS,7aRS)-4,4-diphenylperhydrothiopyrano[2,3-c]pyrrole 1,1-dioxide hydrochloride in 10 cm³ of dichloromethane. After stirring for 1 hour at 0° C. and then 1 hour at 20° C., the reaction mixture is diluted with 10 cm³ of dichloromethane, washed twice with 30 cm³ of distilled water, dried over magnesium sulphate and concentrated to dryness under reduced pressure (2.7 kPa). The oil obtained is crystallized from 30 cm³ of ethyl ether, the crystals are drained and dried. 0.50 g of (4aRS,7aRS)-4,4-diphenyl-6-phenylacetylperhydrothiopyrano[2,3-c]pyrrole 1,1-dioxide is obtained in the form of white crystals.

Infrared spectrum (characteristic bands cm⁻¹): 3050, 3025, 2970, 2930, 1880, 1630, 1595, 1495, 1455, 1425, 1330, 1305, 1140, 1120, 765, 755, 700, 510.

Proton NMR spectrum (DMSO-d₆+CF₃COOD, main signals, a mixture of the two rotamers is observed at room temperature): 2.48 (mt, 1H, CH₂ at 3); 2.8 (mt, 1H, 1H at 5); 3.39 and 3.65 (s and ab J=14, 2H, N—CO—CH₂); 6.9 to 7.6 (mt, 15H, aromatics).

Example of Use 13

1.16 cm³ of triethylamine are added dropwise to a suspension of 1.5 g of (4aRS,7aRS)-4,4-diphenylperhydrothiopyrano[2,3-c]pyrrole 1,1-dioxide hydrochloride and 0.95 g of 1-ethoxy-1-imino2-(2-methoxyphenyl)ethyl hydrochloride in 15 cm³ of 1,2-dichloroethane. After stirring for 20 hours at 20° C., 30 cm³ of dichloromethane are added to the mixture and it is then washed successively with 100 cm³ of water and 100 cm³ of a 5% aqueous solution of potassium carbonate. The organic phase is dried over magnesium sulphate, and concentrated to dryness under reduced pressure (2.7 kPa). The residue is crystallized from an acetonitrile and diisopropyl oxide mixture. The crystals are washed with acetonitrile and then with diisopropyl oxide, drained and dried. 0.83 g of (4aRS,7aRS)-1-imino-2-(2-methoxyphenyl)-6-ethyl4,4-diphenylperhydrothiopyrano[2,3-c] pyrrole 1,1-dioxide is obtained in the form of white crystals; melting point 240° C.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Thiopyranopyrrole derivative comprising the formulas:

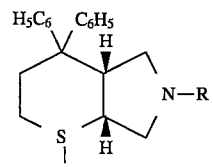

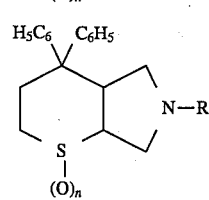

or

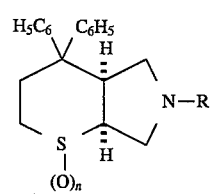

in which the symbol R represents a hydrogen atom, an allyl radical or a radical of the structure:

—CR$_a$R$_b$R$_c$ in which $R_a$ and $R_b$ are hydrogen atoms or phenyl radicals which are optionally substituted (by a halogen atom, an alkyl, alkoxy or nitro radical), and $R_c$ is defined as $R_a$ and $R_b$ or represents an alkyl or alkoxyalkyl radical, at least one of $R_a$, $R_b$ and $R_c$ being a phenyl radical, and the symbol n represents an integer from 0 to 2, it being understood that the above-mentioned alkyl radicals contain 1 to 4 carbon atoms in a linear or branched chain, as well as its pharmaceutically acceptable salts when these exist and it being understood that said thiopyranopyrrole derivative includes the (4aR, 7aR) form or of the (4aS,7aS) form in a pure state, or in the form of a mixture of the cis- (4aRS,7aRS) forms and when n=1, the axial or equatorial stereoisomers at the level of the S-oxide and the position-1 R and S derivatives and mixtures thereof.

2. 4,4-Diphenylperhydrothiopyrano [2,3-c]pyrrole, as well as its pharmaceutically acceptable salts, in the (4aR, .7aR) form or of the (4aS,7aS) form in a pure state, or in the form of a mixture of the cis- (4aRS,7aRS) forms and, the axial or equatorial stereoisomers at the level of the s-oxide and the position-1 R and S derivatives and mixtures thereof.

3. 4,4-Diphenylperhydrothiopyrano[2,3-c]pyrrole 1-oxide, as well as its pharmaceutically acceptable salts, in the (4aR,7aR) form or of the (4aS,7aS) form in a pure state, or in the form of a mixture of the cis- (4aRS,7aRS) forms and, the axial or equatorial stereoisomers at the level of the S-oxide and the position-1 R and S derivatives and mixtures thereof.

4. 4,4-Diphenylperhydrothiopyrano[2,3-c]pyrrole 1,1-dioxide, as well as its pharmaceutically acceptable salts, in the (4aR,7aR) form or of the (4aS,7aS) form in a pure state, or in the form of a mixture of the cis- (4aRS,7aRS) forms and, the axial or equatorial stereoisomers at the level of the S-oxide and the position-1 R and S derivatives and mixtures thereof.

5. 4,4-Diphenyl-6-vinyloxycarbonylperhydrothiopyrano [2,3-c]pyrrole in the (4aR,7aR) form or of the (4aS,7aS) form in a pure state, or in the form of a mixture of the cis- (4aRS,7aRS) forms and, the axial or equatorial stereoisomers at the level of the S-oxide and the position-1 R and S derivatives and mixtures thereof.

6. 4,4-Diphenyl-6-tert-butyloxycarbonylperhydrothiopyrano[2,3-c]pyrrole 1-oxide in the (4aR,7aR) form or of the (4aS,7aS) form in a pure state, or in the form of a mixture of the cis- (4aRS,7aRS) forms and, the axial or equatorial stereoisomers at the Level of the S-oxide and the position-1 R and S derivatives and mixtures thereof.

* * * * *